*(12)* United States Patent
Keil et al.

(10) Patent No.: US 9,192,457 B2
(45) Date of Patent: Nov. 24, 2015

(54) VETERINARY PROCEDURE TABLE

(75) Inventors: Charles C. Keil, Fort Collins, CO (US); John A. Owczarczak, Lancaster, NY (US)

(73) Assignee: MIDMARK CORPORATION, Versailles, OH (US)

( * ) Notice: Subject to any disclaimer, the term of this patent is extended or adjusted under 35 U.S.C. 154(b) by 2024 days.

(21) Appl. No.: 12/102,425

(22) Filed: Apr. 14, 2008
(Under 37 CFR 1.47)

(65) Prior Publication Data

US 2009/0255483 A1   Oct. 15, 2009

(51) Int. Cl.
*A61G 13/06* (2006.01)
*A61D 3/00* (2006.01)
*A61B 19/00* (2006.01)

(52) U.S. Cl.
CPC . *A61D 3/00* (2013.01); *A61B 19/26* (2013.01); *A61G 13/06* (2013.01)

(58) Field of Classification Search
CPC ...................................... A61G 13/06
USPC ................ 5/611, 600, 607–608; 119/753
See application file for complete search history.

(56) References Cited

U.S. PATENT DOCUMENTS

| | | |
|---|---|---|
| 859,696 A | 7/1907 | Schmidt |
| 1,900,255 A | 3/1933 | Ormsbee |
| 2,460,857 A | 2/1949 | Sweat |
| 2,471,140 A | 5/1949 | Breth |
| 2,630,099 A | 3/1953 | Voigt |
| 2,663,929 A | 12/1953 | Carpenter |
| 3,208,432 A | 9/1965 | Fisk |
| 3,302,022 A | 1/1967 | Brenner et al. |
| 3,330,258 A | 7/1967 | Rosenberg |
| 3,473,173 A | 10/1969 | Maciulaitis et al. |
| 3,486,175 A | 12/1969 | Schwartz |
| 3,608,462 A | 9/1971 | Groshong |
| 3,633,901 A | 1/1972 | Lindquist |
| 3,694,830 A | 10/1972 | Koller |
| 3,797,819 A | 3/1974 | Platz et al. |
| 3,810,263 A | 5/1974 | Taylor et al. |
| 3,965,501 A | 6/1976 | Bucher |

(Continued)

FOREIGN PATENT DOCUMENTS

| | | |
|---|---|---|
| EP | 0 293 760 A2 | 12/1988 |
| FR | 2 670 097 A1 | 6/1992 |

(Continued)

OTHER PUBLICATIONS

"Introducing the No Clog T-Trap", web page of http://www.ttrap.com, dated Jan. 16, 2004.

(Continued)

*Primary Examiner* — Fredrick Conley
(74) *Attorney, Agent, or Firm* — Frost Brown Todd LLC

(57) ABSTRACT

A veterinary procedure table includes a vertically extending frame and an animal support assembly upon which an animal may be placed during the performance of a veterinary procedure. An equipment support is secured to the animal support assembly or the vertically extending frame. The equipment support adjustably supports a device or surgical tool used during veterinary procedures performed on an animal placed on the animal support assembly. In one embodiment, a video display is associated with the vertically extending frame for viewing of a particular region on the animal.

2 Claims, 4 Drawing Sheets

(56) References Cited

U.S. PATENT DOCUMENTS

| | | | |
|---|---|---|---|
| 3,971,538 A | 7/1976 | Marvich | |
| 4,029,094 A | 6/1977 | Winicki | |
| 4,073,240 A | 2/1978 | Fly | |
| 4,103,373 A | 8/1978 | Luedtke et al. | |
| 4,113,218 A | 9/1978 | Linder | |
| 4,170,961 A | 10/1979 | Rosenberg et al. | |
| 4,195,829 A | 4/1980 | Reser | |
| 4,340,012 A | 7/1982 | Gustafson | |
| 4,393,969 A | 7/1983 | Woell | |
| 4,454,628 A | 6/1984 | Olson | |
| 4,544,214 A | 10/1985 | Nizel et al. | |
| RE32,052 E | 12/1985 | Rosenberg et al. | |
| 4,558,847 A | 12/1985 | Coates | |
| 4,572,493 A | 2/1986 | Hubert | |
| 4,578,833 A | 4/1986 | Vrzalik | |
| 4,793,428 A | 12/1988 | Swersey | |
| 4,836,144 A | 6/1989 | Cole | |
| 4,872,657 A | 10/1989 | Lussi | |
| 4,885,998 A | 12/1989 | Span et al. | |
| 4,912,754 A | 3/1990 | Van Steenburg | |
| 5,050,253 A | 9/1991 | Wasek | |
| 5,156,166 A | 10/1992 | Sebring | |
| 5,186,337 A * | 2/1993 | Foster et al. | 211/26 |
| 5,224,680 A | 7/1993 | Greenstein et al. | |
| 5,230,109 A | 7/1993 | Zaccai et al. | |
| 5,230,112 A * | 7/1993 | Harrawood et al. | 5/607 |
| 5,244,433 A | 9/1993 | Utterback | |
| 5,269,030 A | 12/1993 | Pahno et al. | |
| 5,271,113 A | 12/1993 | White | |
| 5,305,481 A | 4/1994 | Nebb | |
| 5,443,017 A | 8/1995 | Wacker et al. | |
| 5,526,823 A | 6/1996 | Wheeler et al. | |
| 5,528,782 A | 6/1996 | Pfeuffer et al. | |
| 5,662,069 A | 9/1997 | Smith | |
| 5,715,548 A | 2/1998 | Weismiller et al. | |
| 5,794,570 A | 8/1998 | Foster et al. | |
| 5,802,640 A | 9/1998 | Ferrand et al. | |
| 5,826,286 A | 10/1998 | Cranston | |
| 5,862,549 A | 1/1999 | Morton et al. | |
| 5,867,847 A | 2/1999 | Klawitter et al. | |
| 5,888,190 A | 3/1999 | Meyer et al. | |
| D410,084 S | 5/1999 | Tumey et al. | |
| 5,903,940 A | 5/1999 | Volker et al. | |
| 5,927,745 A | 7/1999 | Cunningham | |
| 5,940,911 A | 8/1999 | Wang | |
| 6,089,242 A | 7/2000 | Buck | |
| 6,101,956 A | 8/2000 | Keil | |
| 6,155,439 A | 12/2000 | Drauhgn | |
| D439,670 S | 3/2001 | Sommer | |
| 6,230,657 B1 | 5/2001 | Read | |
| 6,279,510 B1 | 8/2001 | Batterton | |
| 6,282,736 B1 | 9/2001 | Hand et al. | |
| 6,435,110 B1 | 8/2002 | Keil | |
| 6,467,112 B1 * | 10/2002 | Cheng | 5/606 |
| 6,471,167 B1 | 10/2002 | Myers et al. | |
| 6,477,725 B1 | 11/2002 | Hong et al. | |
| 6,484,334 B1 | 11/2002 | Borders et al. | |
| 6,499,160 B2 | 12/2002 | Hand et al. | |
| 6,553,943 B1 | 4/2003 | Murphy | |
| 6,575,653 B1 | 6/2003 | Krauter | |
| 6,658,680 B2 | 12/2003 | Osborne et al. | |
| 6,711,757 B2 * | 3/2004 | Peck | 4/516 |
| 6,788,018 B1 | 9/2004 | Blumenkranz | |
| 6,804,581 B2 | 10/2004 | Wang et al. | |
| 6,904,621 B2 | 6/2005 | Otto et al. | |
| 6,912,959 B2 | 7/2005 | Kolody et al. | |
| 6,933,695 B2 | 8/2005 | Blumenkranz | |
| 7,032,840 B2 | 4/2006 | Freidell | |
| 7,073,464 B2 * | 7/2006 | Keil | 119/753 |
| 2003/0024485 A1 | 2/2003 | Freidell | |
| 2006/0201448 A1 | 9/2006 | Keil | |
| 2007/0125314 A1 | 6/2007 | Keil | |
| 2007/0245977 A1 | 10/2007 | Keil | |

FOREIGN PATENT DOCUMENTS

| | | |
|---|---|---|
| GB | 981280 | 1/1965 |
| JP | 2003 180184 A | 7/2003 |

OTHER PUBLICATIONS

Veterinary Economics, vetguide.com Illustrated Buyer's Guide to New Equipment and Supplies, Wet Lift Table, web page of http://vetguide.ims.ca, dated Sep. 19, 2005.

Fairbanks Scales, Inc., Fairbanks Vet Scale Operating/User Manual, Issue #2, dated Mar. 2004.

European Patent Office; Search Report and Written Opinion in European Patent Application No. EP09251081 dated Jul. 23, 2009.

* cited by examiner

VETERINARY PROCEDURE TABLE

TECHNICAL FIELD

The present invention relates to tables for examining and performing procedures on animals, and more particularly to a veterinary procedure table with an equipment support.

BACKGROUND

Veterinary examination and procedure tables are known in the art and are convenient for supporting pets and other animals during examination and treatment. Many veterinary tables have a fixed-height animal support surface. Because the height of the animal support surface cannot be adjusted, it is difficult to lift large animals onto the support surface of fixed-height examination tables, particularly after the animal has been anesthetized. Other veterinary examination tables have adjustable-height animal support surfaces, but these generally include some type of support structure directly beneath the table that limits the minimum height to which the table can be adjusted above the floor surface. Moreover, support structure located directly beneath the table may impede the ability of practitioners to draw close to the table while in a seated position.

During certain procedures, such as cutting and trimming of hair and nails, administering shots, suturing wounds, or performing dental work, it may be desired to collect fluid materials discharged from the animal or otherwise used during the procedure and to direct these fluids away from the animal support surface to an appropriate drain. For example, the treatment of wounds, the performance of surgery, or various other veterinary procedures may require irrigation or washing of the animal which generates fluids that should be directed away from the animal support surface. As an additional example, prophylactic cleaning and various other dental treatments are becoming increasingly popular, particularly for pets. Such dental procedures necessarily require the use of fluids for washing and irrigation, as discussed above. Accordingly, veterinary examination or treatment tables may be provided with a sink, or basin, adapted to collect fluids generated during treatment and to direct these fluids to an appropriate drain. Conventional wet procedure tables, however, are not generally configured for height adjustment.

In any case, the practitioner must have surgical or examination tools and equipment available for performing the necessary or requested procedures. These tools are usually arranged on separate stands or racks and positioned proximate the table. Consequently, multiple, separate stands may be required for even moderately complex procedures. The practitioner may then become surrounded by a disarranged cluster of stands. In addition, the tools or equipment, while on their respective stands, are generally positioned after placing the animal on the table. Arrangement or preparation of these tools may require additional support staff and preparation time. In certain instances, such as following traumatic injury to the animal when time is of the essence, the additional staff or time may be unavailable. Therefore, the subject animal may not receive the practitioner's immediate and full attention.

A need therefore exists for an improved veterinary procedure table that overcomes these and other drawbacks of the prior art.

SUMMARY

The present invention overcomes the foregoing and other shortcomings and drawbacks of veterinary procedure tables heretofore known for use in examining or treating animals. While the invention will be described in connection with certain embodiments, it will be understood that the invention is not limited to these embodiments. On the contrary, the invention includes all alternatives, modifications and equivalents as may be included within the spirit and scope of the present disclosure.

According to one embodiment of the present disclosure, a veterinary procedure table comprises a vertically extending frame, an animal support assembly, and an equipment support. The animal support assembly has first and second spaced apart ends defining a lengthwise dimension and first and second spaced apart sides defining a widthwise dimension, wherein the lengthwise dimension is greater than the widthwise dimension. The animal support assembly is slidably coupled to the vertically extending frame only at the first end such that the animal support assembly is cantilevered from the vertically extending frame with the second end extending outwardly from the vertically extending frame. The animal support assembly is movable to a plurality of elevations relative to the vertically extending frame. The equipment support is movably coupled to the vertically extending frame or the animal support assembly. The equipment support includes a proximal end secured to the animal support assembly or the vertically extending frame and a distal end adapted to adjustably support a device or surgical tool used during veterinary procedures performed on an animal placed on the animal support assembly.

In another embodiment, the veterinary procedure table comprises a vertically extending frame, an animal support assembly, and a video display associated with the vertically extending frame. The video display is in electrical communication with a device or surgical tool. The video display is adapted to provide visual images taken with the device or surgical tool during procedures performed on an animal supported by the animal support assembly.

BRIEF DESCRIPTION OF THE FIGURES

The accompanying drawings, which are incorporated in and constitute a part of this specification, illustrate exemplary embodiments of the invention and, together with a general description given above, and the detailed description given below, serve to explain the invention in sufficient detail to enable one of ordinary skill in the art to which the invention pertains to make and use the invention.

DETAILED DESCRIPTION

Figure 1:
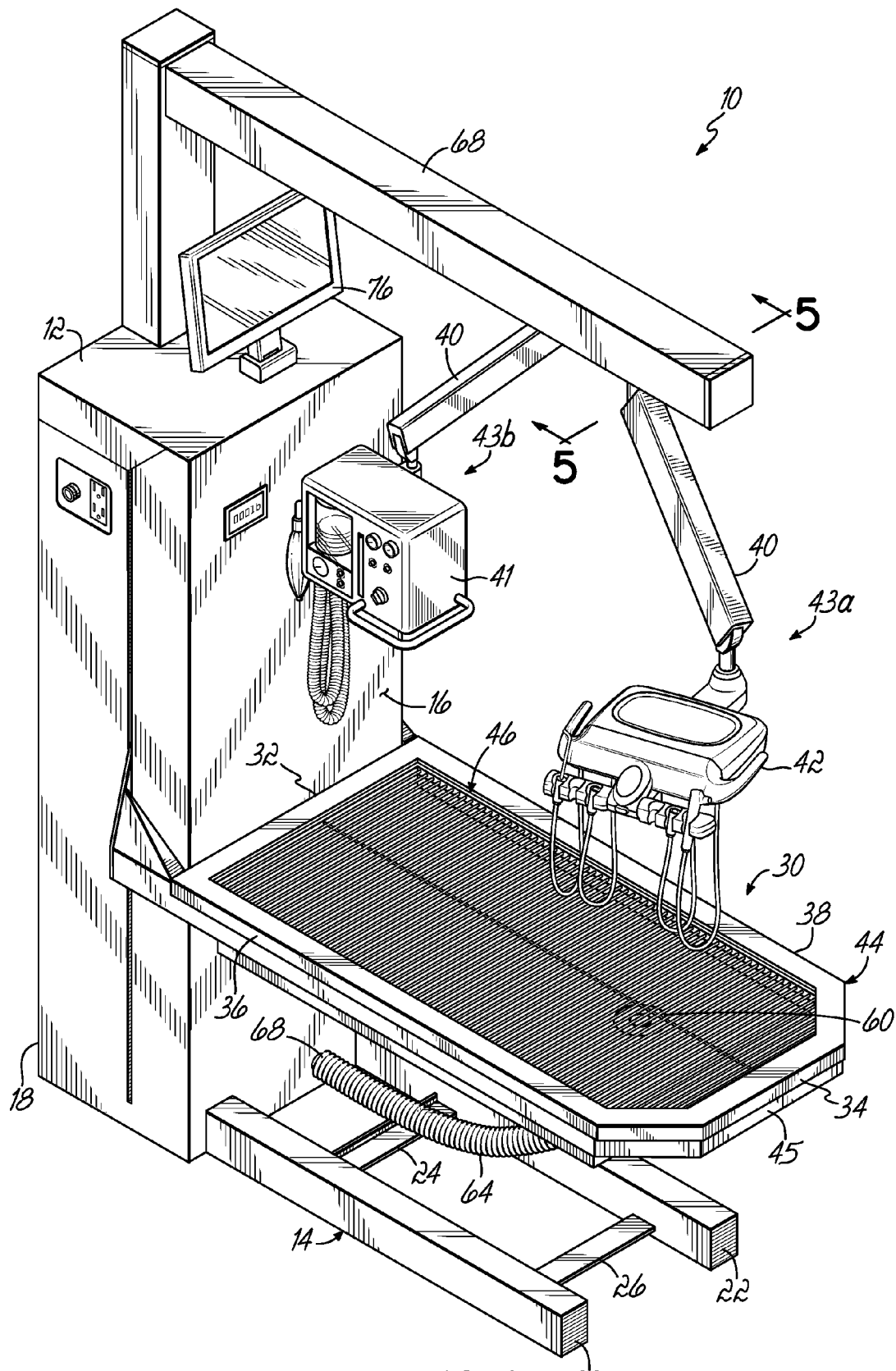
FIG. 1 is a perspective view of an exemplary height-adjustable veterinary procedure table in accordance with the principles of the present invention.
Figure 2:
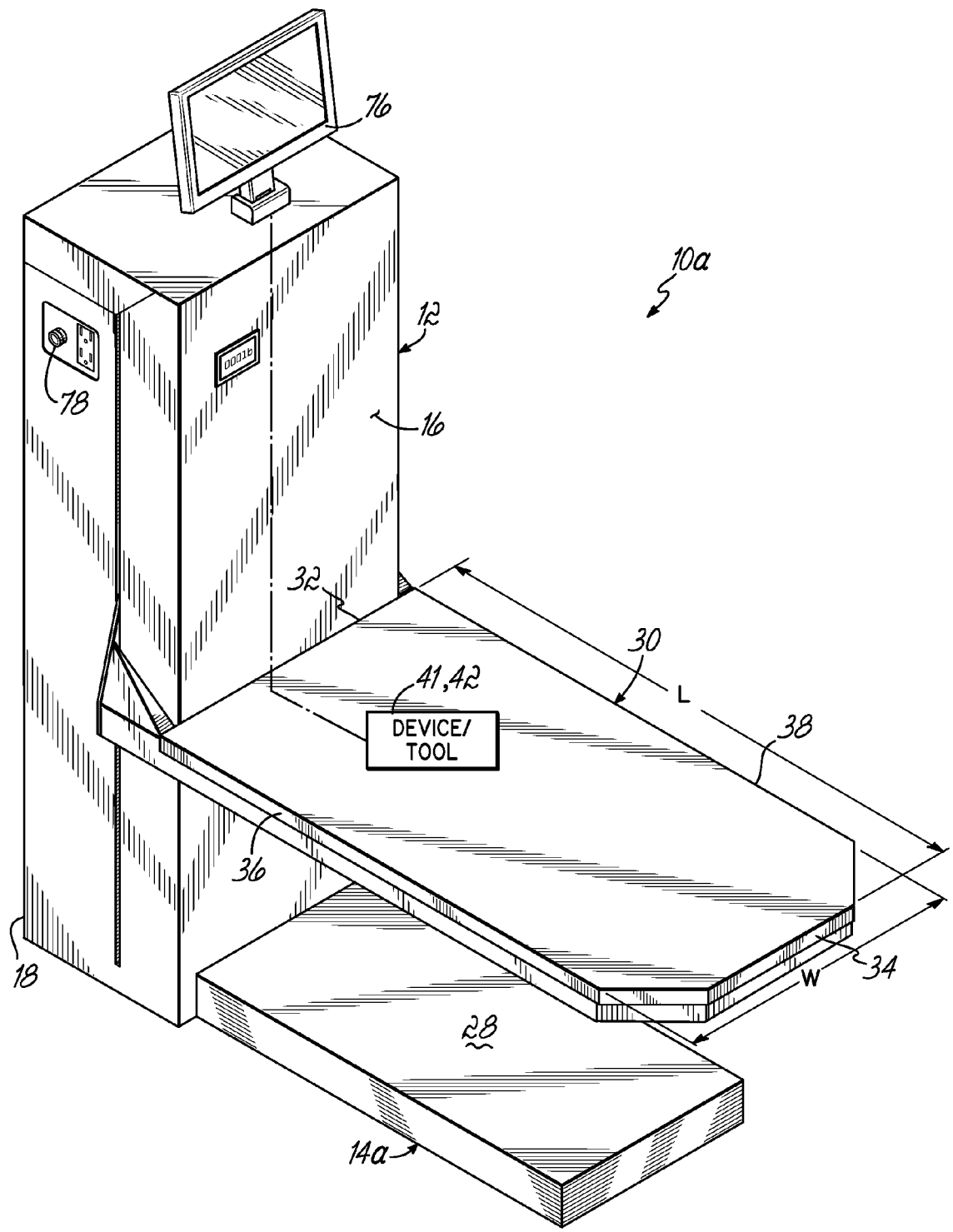
FIG. 2 is a perspective view of another embodiment of a height-adjustable veterinary procedure table in accordance with another aspect of the invention.

FIGS. 1 and 2 depict exemplary veterinary procedures table 10, 10a in accordance with the principles of the present disclosure. The veterinary procedure table 10, 10a includes a vertically extending frame 12 extending generally upwardly from a floor surface, and a base assembly 14 coupled to the vertically extending frame 12 at a lower end thereof. The vertically extending frame 12 includes a structural frame (not shown) housed within an enclosure comprising a front cover 16 and a rear cover 18. The vertically extending frame 12 is generally described in U.S. Pat. No. 7,073,464 to Keil, and the details of such are not repeated herein. The base assembly 14 may include first and second elongate supports 20, 22 extending outwardly from the vertical frame assembly, and one or more transverse members 24, 26 extending between the supports 20, 22, as shown in FIG. 1 and described in U.S. Pat. No. 7,073,464. As shown in FIG. 2, the base assembly 14a may include a solid support 28. In any case, the base assembly 14, 14a extends outwardly from the vertically extending frame 12 and helps to maintain stability of the veterinary procedure table 10, 10a.

The veterinary procedure table 10, 10a further includes an animal support assembly 30a cantilevered outwardly from the vertically extending frame 12 and slidably coupled to the vertically extending frame 12 for selective height adjustment relative to the floor surface. As illustrated in FIG. 2, the animal support assembly 30 includes first and second spaced apart ends 32, 34 defining a lengthwise dimension (L), and first and second spaced apart sides 36, 38 defining a widthwise dimension (W). The lengthwise dimension (L) is greater than the widthwise dimension (W) such that the animal support assembly 30 is cantilevered longitudinally away from the vertically extending frame 12, with the second end 34 extending outwardly from the vertically extending frame 12. While not shown in FIG. 1, it will be observed that the same dimensions (L and W) apply to the embodiment of the veterinary procedure table 10 illustrated in FIG. 1.

The animal support assembly 30 is coupled to the vertically extending frame 12 only at the first end 32. This arrangement eliminates any support structure directly beneath the animal support assembly 30 and facilitates movement of the animal support assembly 30 to a height that is very close to the floor surface. Moreover, the absence of support structure directly beneath the animal support assembly 30 allows practitioners to be seated adjacent the animal support assembly 30 with their legs extending beneath the animal support assembly 30. Accordingly, the veterinary procedure table 10 conveniently allows practitioners to be seated very close to an animal supported on the animal support assembly 30 during the performance of procedures.

In use, the animal support assembly 30 may be moved to a position close to the floor surface to facilitate placing an animal onto the veterinary procedure table 10. The animal support assembly 30 may thereafter be raised vertically upward to any height desired by the practitioner.

Figure 3:
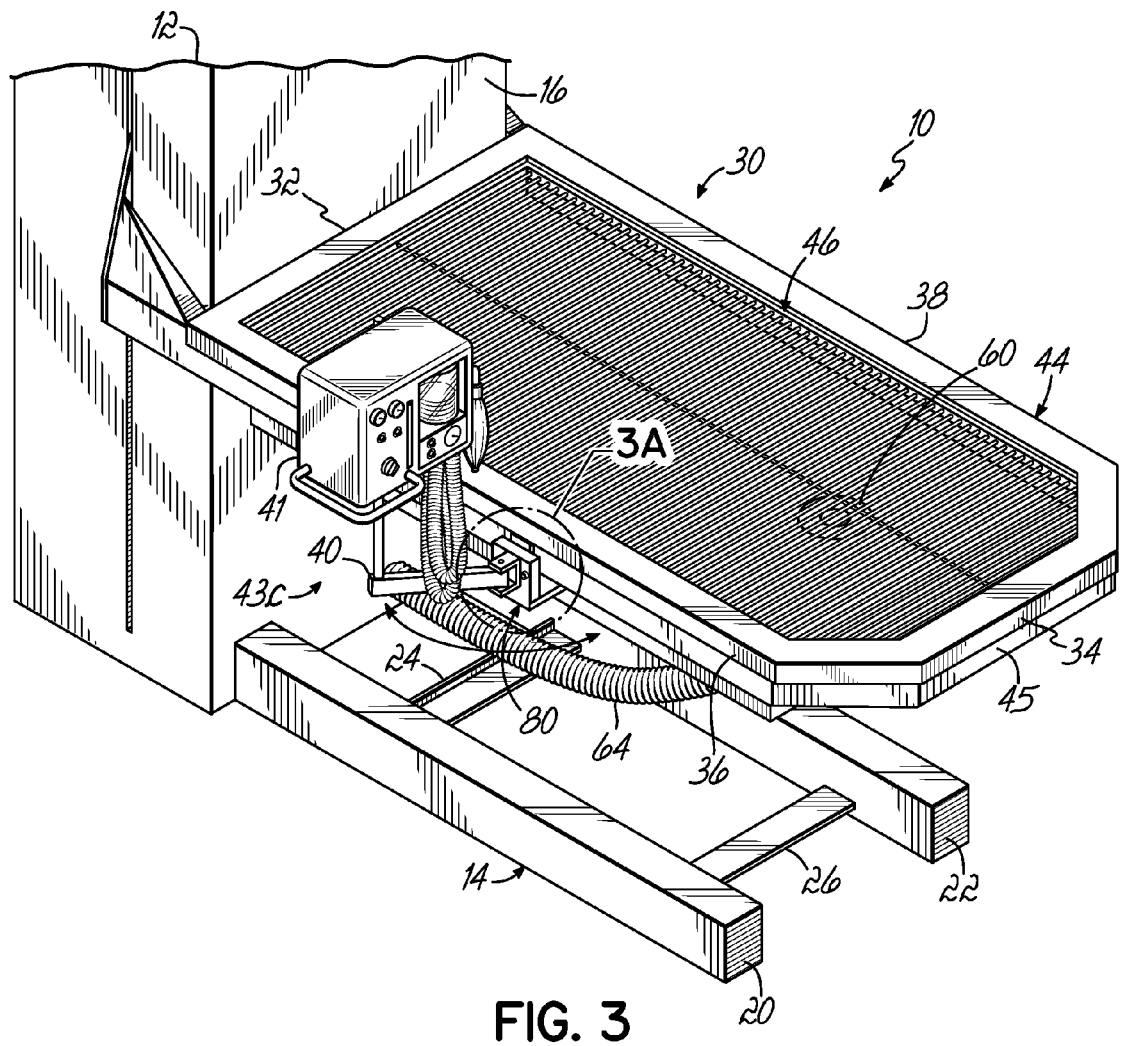
FIG. 3 is a partial perspective view of another embodiment of a veterinary procedure table illustrating an equipment support secured to an animal support assembly.

As shown in FIGS. 1 and 3, in one embodiment, the veterinary procedure table 10 includes at least one equipment support 40. The equipment support 40 is a structure for holding one or more devices 41 or surgical tool 42 in an easily accessible position relative to the animal support assembly 30. Thus, the practitioner may easily access the device 41 or surgical tool 42 held by the equipment support 40 while positioned to perform a procedure on an animal on the animal support assembly 30. The equipment support 40 of FIG. 1 may have, for example, a tool tray such that various surgical, dental, or other hand-held tools (e.g. a dental examination instrument, a periodontal scaler, a scalpel, or a drill) may be arranged on the tool tray for easy access by the practitioner. It will be appreciated that the tools may be operatively attached to the tool tray or equipment support 40. For example, dental drills and polishers may require an air or other power source and other utilities such as water or vacuum for proper operation. Moreover, as will be discussed in more detail later, electricity, air, water, vacuum or various other utilities may be provided at least in part through the equipment support 40. In addition, or alternatively, the equipment support 40 may have a device 41 secured thereto. For example, the device 41 may be a diagnostic tool, such as an anesthesia machine, a blood pressure monitor, a heart rate monitor, or any other device that might be used during the performance of a procedure on an animal.

In the embodiments shown, the equipment support 40 may be coupled to a portion of the vertically extending frame 12 such that it may project over the animal support assembly 30 (shown in FIG. 1), or the equipment support 40 may be coupled to the animal support assembly 30 (shown in FIG. 3). It will be appreciated that the equipment support 40 coupled to the vertically extending frame 12 does not move when the animal support assembly 30 is raised and lowered. In contrast, an equipment support 40 that is coupled to the animal support assembly 30 will move with the animal support assembly 30 as the animal support assembly 30 is raised and lowered. The placement of the equipment support 40 may depend on the size and weight of the device 41 or surgical tool 42 supported, the sensitivity of the device 41 or surgical tool 42 to vibration or impact (e.g. from a paw, hoof, or tail), or simply according to the practitioner's preferences. While FIGS. 1 and 3 depict equipment supports 40 secured to a portion of the vertically extending frame 12 or alternatively to the animal support assembly 30, one skilled in the art will recognize that both types of equipment supports 40 may be utilized in combination, by securing at least one equipment support 40 to each of the animal support assembly 30 and the vertically extending frame 12.

The equipment support 40 may be rigidly connected to the animal support assembly 30 or the vertically extending frame 12. Alternatively, the equipment support 40 may incorporate one or more joints 43 (as shown in FIGS. 1 and 3) such that the practitioner may move the device 41 or surgical tool 42, as previously described, to one or more desired positions. It will be appreciated that not only does articulation of the equipment support 40 facilitate positioning of the device 41 or surgical tool 42 within reach of the practitioner or proximate to the animal, articulation may allow the practitioner to move expensive diagnostic equipment and sterile tools away from a nervous or an uncontrollable animal until an anesthetic is administered to render the animal unconscious. Therefore, large animals may be pulled or coaxed onto the animal support assembly 30 while the animal support assembly 30 is positioned near the floor without concern that the animal may become unexpectedly excited or anxious and damage equipment prior to the practitioner restraining the animal or administering anesthetic.

Figure 4:
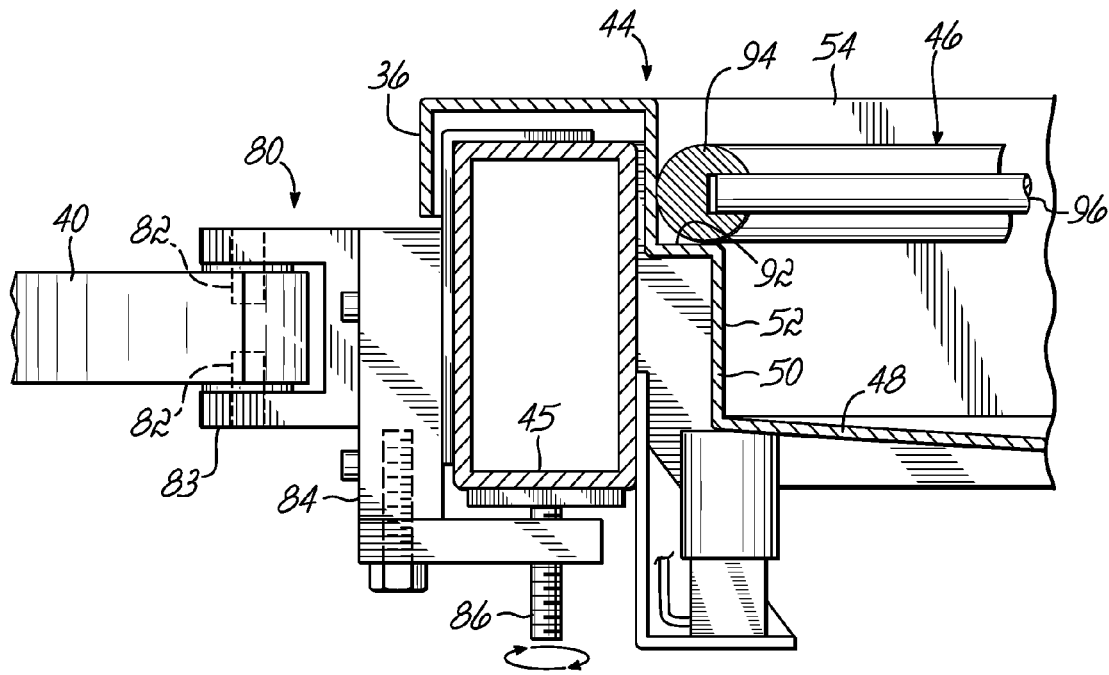
FIG. 4 is a cross-sectional view taken along section line 4-4 of FIG. 3A.

With continued reference to FIGS. 1 and 3, in one embodiment, the animal support assembly 30 further comprises a sink 44 removably supported atop an animal support frame 45. A grille 46 is associated with the animal support frame 45 and is positioned above the sink 44. The sink 44 is sized and shaped to be received within the animal support frame 45. With reference now to FIG. 4, the sink 44 includes a bottom wall 48 and one or more sidewalls 50 defining a reservoir 52 with an open, upper end 54. The bottom wall 48 may be sloped to direct fluid material and debris passing through the grille 46 and received in the reservoir 52 toward a drain 60 shown in FIGS. 1 and 3. The drain 60 may be coupled to a conduit 64 for removing fluids from the sink 44 and directing the fluids to an appropriate receptacle. In the embodiment shown, the conduit 64 is coupled to a fluid inlet 68 (shown best in FIG. 1) provided in the vertically extending frame 12, whereby fluid material from the sink 44 may be pumped to an appropriate waste drain as described in U.S. Pat. No. 7,073,464. It will be appreciated, however, that various other methods and structure suitable for collecting and removing fluid material from the drain 60 of the sink 44 may be used.

With continued reference to FIG. 1, in another aspect, a cantilever member 68 is secured to the vertically extending frame 12. The cantilever member 68 projects over the animal support assembly 30. In the embodiment shown, the cantilever member 68 is generally aligned with the animal support assembly 30. Thus, when the equipment support 40 is attached to the cantilever member 68, the device 41 and/or surgical tool 42 supported thereby may be accessible to the practitioner poised to perform procedures on an animal positioned on the animal support assembly 30. Similar to the equipment support 40 previously described, if the equipment support 40 is attached to the cantilever member 68 via one or more joints 43, the device 41 or surgical tool 42 supported thereby may be relocated before, during, and after procedures. However, it will be appreciated that the device 41 or surgical tool 42 secured to the cantilever member 68 remain stationary while the animal support assembly 30 is raised and lowered.

Figure 5:
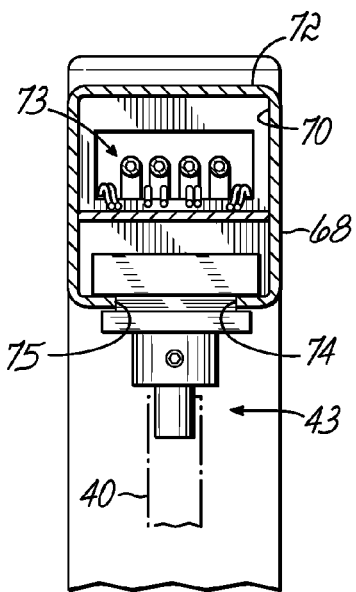
FIG. 5 is a cross-section view taken along section line 5-5 of FIG. 1.

In one embodiment, as shown in a cross-sectional view of FIG. 5, the cantilever member 68 has a passage 70 passing therethrough. In the embodiment depicted, the passage 70 is formed by one or more tubular members 72 such that the passage 70 is fully enclosed. Moreover, one or more utility service lines 73, may be positioned within the tubular member 72 to provide electricity, water, air, vacuum, data signals, or other utility services or combinations thereof, proximate the animal support assembly 30. In one embodiment, one or more of the above mentioned wires or tubes 73 operatively connect to one or more devices 42 or surgical tool 42 supported by the equipment support 40 (shown in FIG. 1) at one end and connect to a respective supply (not shown) at the other end, which may or may not be supplied by or through vertically extending frame 12. One skilled in the art will appreciate that enclosing the above-mentioned wires and tubes 73 may provide a more sterile or cleanable environment. However, it will be appreciated that the passage 70 may alternatively be formed by a C-shaped member, with or without a removable cover, (not shown) or other open structure such that the wires and tubes 73 are easily accessible. Therefore, one or more devices 41 or surgical tool 42 may be added or swapped with another device 41 or surgical tool 42 having different power, utility, or connectivity requirements, and those different power, utility or connectivity requirements may be quickly added by running the necessary cables and such within the passage 70 without disassembly of the veterinary procedure table 10.

With continued reference to FIGS. 1 and 5, one or more equipment supports 40 may be slidably received by the cantilever member 68. For example, as shown in FIG. 5, a portion of the equipment support 40 may have a recess 74 that cooperates with a channel 75 in the cantilever member 68. Therefore, the equipment support 40 may slide or otherwise be moved toward or away from the vertically extending frame 12 along the cantilever member 68. It will be appreciated, however, that various other methods and structure suitable for adjustably securing the equipment support 40 to the cantilever member 68 may be used.

In yet another exemplary embodiment, the veterinary procedure table 10, 10a comprises a video display 76, shown in FIGS. 1 and 2, associated with the vertically extending frame 12. The video display 76 may be in operative communication with one or more devices 41 or surgical tool 42, discussed above. Therefore, for example, the veterinary procedure table 10 may contain electrical wiring to accept plug-ins at a plug-in interface 78 for blood pressure, temperature, and/or other vital signs readout on the video display 76. Other tools may operatively connect with the video display 76 via a wire or wireless connection (as depicted by the phantom line from the device 41 or surgical tool 42 to the video display 76), including for example, one of a variety of endoscopes or an otoscope. Additionally, the video display 76 may be operatively connected to one or more endoscopes, otoscopes, or cameras supported by the equipment support 40 via one or more video cables passing through the passage 70 shown in FIG. 5. The video display 76 may advantageously facilitate shared viewing of a particular region on the animal with other persons in the room with the practitioner.

In one embodiment, the video display 76 may be remotely controlled to freeze one or more views of a portion of the animal so that the practitioner may discuss elective surgeries with the animal's owner and thereby enhance revenue for the practitioner's practice. In another embodiment, the video display 76 may be operatively connected to a printer (not shown) or storage device (not shown) for saving the images taken for further review or sharing with others. As previously described and with reference to FIGS. 3 and 4, the animal support assembly 30 may include a grille 46 that is received within the upper end 54 of sink 44 for supporting an animal directly over the reservoir 52 of the sink 44. With reference specifically to FIG. 4, a ledge 92 may extend around the inner periphery of the sink 44, near the upper end 54, for supporting the grille 46 thereon. The grille 46 comprises outer peripheral frame members 94 and a plurality of spaced transverse rods 96 extending between the frame members 94 for supporting an animal thereon. Because the transverse rods 96 are spaced apart, fluid material from the animal or fluids used during treatment may flow between the rods 96 and into the sink 44. The fluid material is then directed along bottom wall 48 to drain 60, whereafter it is removed from sink 44 through conduit 64.

Figure 3A:
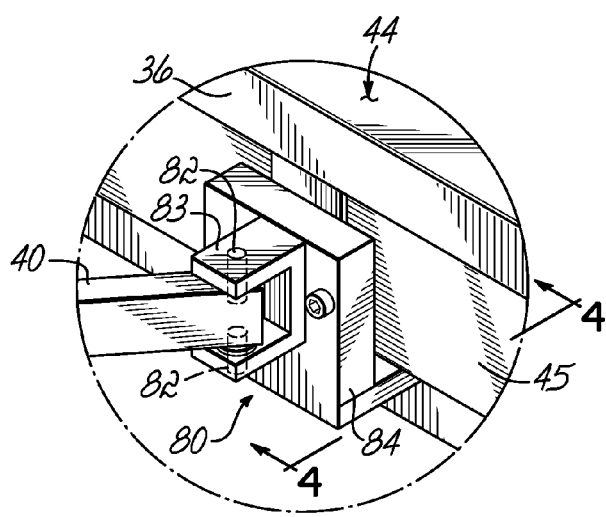
FIG. 3A is an enlarged view of the encircled area 3A of FIG. 3.

One embodiment of a clamping system 80 with the equipment support 40 secured thereto is also depicted in FIGS. 3A and 4. The equipment support 40 may include trunnions 82 captured within a yoke 83 for further attachment to the clamping system 80. With reference to FIG. 4, the clamping system 80 may include a C-shaped bracket 84 that operates in cooperation with a threaded member 86. In operation, the equipment support 40 may be secured to the animal support frame 45 by rotating the threaded member 86 thereby frictionally engaging a portion of the animal support frame 45. Accordingly, the equipment support 40 and any attached devices 41 or surgical tool 42 may be positioned at a desired location around the periphery of the animal support assembly 30 by releasing the clamping system 80 and sliding or detaching the equipment support 40 from the animal support assembly 30 and securing the equipment support 40 at another location along the animal support frame 45. It will be appreciated that other clamping or attachment systems may be utilized for securing the equipment support 40 to the animal support assembly 30.

While various aspects in accordance with the principles of the invention have been illustrated by the description of various embodiments, and while the embodiments have been described in considerable detail, they are not intended to restrict or in any way limit the scope of the invention to such detail. The various features shown and described herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of the general inventive concept.

What is claimed is:

1. A veterinary procedure table, comprising:
a vertically extending frame; an animal support assembly having first and second spaced apart ends defining a lengthwise dimension, and having first and second spaced apart sides defining a widthwise dimension, said lengthwise dimension being greater than said widthwise dimension, said animal support assembly slidably coupled to said vertically extending frame only at said first end such that said animal support assembly is cantilevered from said vertically extending frame, with said second end extending outwardly from said vertically extending frame, and such that said animal support assembly is movable from a position very close to a floor surface, such that a large animal can be placed onto the animal support assembly, to a plurality of elevations relative to said vertically extending frame, to raise the animal from the floor surface; a sink associated with said animal support assembly, said sink including a bottom wall and at least one sidewall defining a reservoir adapted to receive fluid or debris;
a grille associated with said animal support assembly and extending over and across said sink, said grille comprising a plurality of spaced-apart rods extending between peripheral frame members and defining a substantially planar structure adapted to support the animal thereon and to pass fluid or debris therethrough into said sink;
an equipment support movably coupled to said vertically extending frame or said animal support assembly, wherein said equipment support includes a proximal end secured to said animal support assembly or said vertically extending frame, and a distal end adapted to adjustably support a device or surgical tool used during veterinary procedures performed on an animal placed on said animal support assembly; and
a cantilever member having a proximal end affixed to said vertically extending frame and a distal end projecting over said animal support assembly, wherein said equipment support is coupled to said cantilever member wherein said cantilever member includes a passage for passing at least one utility service line through said passage to said equipment support.

2. The veterinary procedure table of claim 1, wherein said equipment support includes a first equipment support and a second equipment support, and said device or surgical tool includes a first device or surgical tool coupled to said first equipment support and a second device or surgical tool coupled to said second equipment support.

* * * * *